(12) United States Patent
McCullough et al.

(10) Patent No.: US 12,083,313 B2
(45) Date of Patent: Sep. 10, 2024

(54) PUMP

(71) Applicant: Jacobsen Innovations, Inc., Salt Lake City, UT (US)

(72) Inventors: John McCullough, Salt Lake City, UT (US); Wayco Scroggin, Sandy, UT (US)

(73) Assignee: Jacobsen Innovations, Inc., Salt Lake City, UT (US)

( * ) Notice: Subject to any disclaimer, the term of this patent is extended or adjusted under 35 U.S.C. 154(b) by 703 days.

(21) Appl. No.: 17/264,780

(22) PCT Filed: Aug. 1, 2019

(86) PCT No.: PCT/US2019/044734
§ 371 (c)(1),
(2) Date: Jan. 29, 2021

(87) PCT Pub. No.: WO2020/028709
PCT Pub. Date: Feb. 6, 2020

(65) Prior Publication Data
US 2021/0290842 A1    Sep. 23, 2021

(51) Int. Cl.
*A61M 5/142* (2006.01)
*A61M 39/24* (2006.01)

(52) U.S. Cl.
CPC ........ *A61M 5/14216* (2013.01); *A61M 39/24* (2013.01); *A61M 2039/242* (2013.01); *A61M 2039/248* (2013.01)

(58) Field of Classification Search
CPC .................. A61M 5/142; A61M 39/24; A61M 2039/242; A61M 2039/248; A61M 5/14216; F04B 5/02; F04B 17/03; F04B 35/04
See application file for complete search history.

(56) References Cited

U.S. PATENT DOCUMENTS

| | | | |
|---|---|---|---|
| 5,637,095 A * | 6/1997 | Nason | A61M 5/14244 604/154 |
| 5,941,533 A * | 8/1999 | Jacobsen | F04B 53/164 277/560 |
| 2002/0091358 A1 | 7/2002 | Klitmose | |
| 2003/0044293 A1 | 3/2003 | Gray, Jr. | |
| 2011/0190705 A1 | 8/2011 | Mernoe et al. | |

* cited by examiner

*Primary Examiner* — Michael J Tsai
*Assistant Examiner* — Rachel T. Smith
(74) *Attorney, Agent, or Firm* — MORRISS O'BRYANT COMPAGNI CANNON, PLLC (57) ABSTRACT

A pump comprises a drive mechanism, a tube coupled to the drive mechanism, a filament coupled to the tube and extendable into the tube by the drive mechanism and at least one check valve coupled to the tube. As the filament is forced by the drive mechanism into the tube, fluid contained in the tube is forced by the filament through the at least one check valve and out of the tube.

15 Claims, 8 Drawing Sheets

PUMP

CROSS-REFERENCE TO RELATED APPLICATIONS

This application is a national phase entry under 35 U.S.C. § 371 of PCT/US2019/044734 filed on Aug. 1, 2019, which claims priority to U.S. Provisional Patent Application No. 62/713,401 filed on Aug. 1, 2018, the entirety of each of which is incorporated by this reference.

BACKGROUND

Field of the Invention: The present application generally relates to pumps for precise and controlled delivery of medications or other liquid substances and more specifically to a pump that can provide precise and controlled delivery of medications or other liquid substances continuously or in set intervals at very low dosage rates.

State of the Prior Art: Medical device pumps and systems are relatively well known in the medical arts, for use in delivering or dispensing a prescribed medication or substance such as pain medication, antibiotics or insulin to a patient. One such pump, commonly referred to as an infusion pump, delivers a volumetrically controlled medication to the patient over a period of time. A processing circuitry controls the periodic or continuous delivery of dosages of medication to a patient at predetermined rates. Infusion pumps often contain an electrical motor that rotates a lead-screw; the rotation of the lead-screw causes a nut to linearly move along it. The nut pushes a plunger through a syringe or a cartridge internal to the pump that causes medication to move from the syringe to the patient along the infusion path.

In one form, such devices comprise a pump housing adapted to receive a syringe carrying a prescribed medication for administration to a patient through infusion tubing and an associated catheter or the like. The infusion pump includes a small drive motor connected via a lead screw assembly for motor-driven advancement of a syringe piston plunger to administer the medication to the patient. Programmable controls are normally provided for operating the drive motor continuously or at periodic intervals to obtain a closely controlled and accurate delivery of medication over an extended time period. Such infusion pumps are utilized to administer insulin and other medications, with an exemplary pump construction being shown and described in U.S. Pat. No. 4,562,751 to Nason et al., U.S. Pat. No. 4,678,408 to Nason et al, and U.S. Pat. No. 4,685,903 to Cable et al. U.S. Pat. Nos. 4,562,751, 4,678,408, and 4,685,903 are hereby incorporated herein by reference.

Infusion pumps of the general type described above have provided significant advantages and benefits with respect to accurate delivery of medication over an extended time period. The infusion pump is often designed to be extremely compact and may thus be adapted to be carried by the patient, for example, by means of a belt clip or the like. As a result, important medication can be administered with precision and in an automated manner, without significant restriction on the patient's mobility or life-style.

Certain new drugs, such as biologicals and DNA therapies, coming into the market, however, require a different drug delivery device than conventional infusion pumps for several reasons. Such new drugs require accurate delivery at extremely slow flow rates. For example, a drug may require delivery of 1 mL continuously over 1 day with a total dose accuracy of +/−5% and a flow accuracy of +/−5%. Flow accuracy means from minute to minute the flow does not change more than +/−5% from the required continuous flow rate. In this example, this requires a flow rate of 0.04167 mL/hr or 0.000694 mL/min.

Additionally, for drugs that have a short shelf life at room temperature, each component of the pump that is exposed to the drug, such as the drug reservoir, tubing, pumping components of the pump that come into contact with the drug must be disposed on a daily basis. As such, it is highly advantageous if the disposable components are relatively inexpensive, e.g., less than $50 per day in 2018 US dollars.

Furthermore, such drugs are expensive. As such, the delivery system must be capable of delivering a close to 100% of the drug as possible. As such, the delivery system must be able to deliver to the patient any of the drug contained in the tubing that leads to the patient.

Finally, because some of the patients will be infants, the strapping the drug delivery system to the arm or leg, which can result in tearing the skin of the patient, is not desirable. Thus, the drug delivery system can be mounted away from the patient.

Thus, there is therefore a need for a drug delivery system that in addition to being small, lightweight and low in energy consumption will be able to deliver substantially all of the drug accurately and at a consistent dosage rate over time.

SUMMARY OF THE INVENTION

Accordingly, a pump for precise and controlled delivery of medications or other liquid substances at very low dosage rates is comprised of a filament that is extendable and retractable inside a drug delivery tube. The filament acts as a syringe that can force the flow of a drug inside the tube to a patient. The filament and associated tube acts like a syringe that is driven by a drive mechanism, such as a stepper motor, servo motor or other linear drive device that can accuracy control linear movement of the filament relative to the tube. The drive mechanism may be coupled to a gear box reduction for increased accuracy of filament movement and thus drug delivery accuracy. Specifically, the drive mechanism moves the filament through the tube with linear accuracy.

In one embodiment, the filament includes a scale (e.g., Vernier) printed on its outer surface. The filament can thus act as a linear encoder that can be ready by optical or other sensors to provide feedback of the filament's position relative to the tube and thus confirm the dosage of the drug provided to the patient accordingly.

In another embodiment, the filament engages a secondary wheel that moves as the filament moves, causing the secondary wheel to rotate. The rotation of the secondary wheel confirms that the filament is actually moving and not slipping as the drive mechanism moves the filament.

In one embodiment, a sliding seal is provided between the filament and the proximal end of the tube closest to the drive mechanism. The seal prevents the drug from escaping the proximal end of the tube.

In yet another embodiment, an external seal is provided on the filament, such as a plunger or O-ring on the distal end of the filament farthest from the drive mechanism.

The distal end of the tube is connected to the patient through a bi-directional pressure relief valve. The pressure relief valve may have approximately 5 psi relief.

Alternatively, the distal end of the tube may be connected to a unidirectional relief valve with an additional port through a check valve coupled to a separate fitting where the system can be filled.

It is contemplated that the drive mechanism may be a separate device that is durable with the tube and associated filament being disposable in order to minimize the cost of the disposable components of the system. Alternatively, the drive mechanism may be disposable as well.

The pump of the present invention is coupled to an injection site of the patient. The injection site may be vascular, subcutaneous or other injection site types known in the art. The injection site includes a disconnect fitting to which the pump tube of the present invention connects. The distal end of the pump tube includes a check valve to prevent a flow of fluid from the patient when the pump tube is disconnected.

The pump can either be provided with the drug prefilled in the tube with the filament retracted within the tube or ready to be filled with the filament fully extended into the tube.

To fill the pump, the distal end of the tube is coupled to a vial of the desired drug. The drive mechanism pulls the filament through the tube retracting it into the pump housing thus forming a vacuum in the tube. When the vacuum pressure exceeds the limit of a pressure relief valve, the drug is drawn into the tube behind the distal end of the tube.

Once the tube is completely filled or the drug in the vial has been completely drawn into the tube, the tube is disconnected from the vial. The pump is then ready to be used or can be stored as required by the drug, such as in a refrigerator.

Prefilled pumps with a drug can be placed in packages and stored in a refrigerator so that clinicians can take a package from the refrigerator, open the package, remove the pump/drug system from the package, attached the pump tube to the patient and start the pump.

The pump system of the present invention can be battery powered or externally powered such as with power from a common 115 AC wall socket.

The pump system may include a housing within which are housed the electronics and the drive mechanism. In this case, the housing and all of its components can be dispensed after the pump has been used. Alternatively, the pump housing may contain the electronics and drive mechanism as reusable components with the tubing and filament contained in a separate disposable cartridge that is discarded after a single use.

In one embodiment, the pump utilizes a bi-directional pressure relief valve system comprised of two unidirectional pressure relief valves.

In another embodiment, the pump utilizes a single bi-directional pressure relief valve.

The pressure relief valves can only be triggered at an elevated pressure such that body fluids from the patient cannot leak back into the system.

In yet another embodiment, the pump includes a unidirectional pressure relief valve out with check valve from separate port going in. In this case, the end of the tube has two ports. The unidirectional pressure relief valve out and the check valve in. When the pump arrives with the tube completely filled with the filament, the end of the tube check valve-in-connector is connected to the vial of drug. The drive mechanism pulls the filament backwards through the tube. Due to the use of the check valve, the vacuum required to pull fluid into the tube is directly a function of the pressure rating of the check valve. Once the tube is filled with drug, the check valve in-port is removed from the vial of drug and capped. The pump is now ready to be used or can be stored in a refrigerator or in whatever condition the drug requires. The pump filled with drug can be stock piled in the refrigerator such clinicians administering the drug remove a package from the refrigerator, open the package, remove the pump system from the package, connect the system via the pressure check valve out to the patient and press start.

Another option is to have a unidirectional check valve out to the patient. A separate port is provided that has a mechanically controlled valve that allows for filling the tube. Alternatively, a mechanically controlled device that overrides the output check valve allows fluid to flow into the system.

In another embodiment, the pump comprises a drive mechanism, a first tube coupled to the drive mechanism, a filament coupled to the first tube and extendable into the first tube by the drive mechanism and at least one check valve coupled to the first tube, wherein as the filament is forced by the drive mechanism into the first tube. Fluid contained in the first tube is forced by the filament through the at least one check valve and out of the first tube.

In another embodiment, the drive mechanism comprises a motor coupled to at least one drive wheel, the drive wheel engaging the filament to drive the filament through the first tube.

In another embodiment, a filament seal is positioned proximate a proximal end of the first tube, the filament seal providing a seal around the filament and preventing fluid within the first tube from passing out of the proximal end of the first tube.

In another embodiment, a pump housing comprises a filament container, the filament arranged in a spool of unused filament within the filament container.

In yet another embodiment, a second wheel is positioned proximate the drive wheel with the filament passing between the drive wheel and the second wheel and engaged between the drive wheel and the second wheel such that rotation of the drive wheel causes advancement of the filament and rotation of the second wheel.

In another embodiment, a bi-directional pressure relief valve comprises a first pressure relief valve for inward flow and a second pressure relief valve for outward flow.

In still another embodiment, a uni-directional pressure relief valve is coupled to a distal end of the first tube, the uni-directional pressure relief valve comprising a first pressure relief valve for outward flow through a patient port.

In yet another embodiment, a check valve for inward flow is coupled to a filling port through which the first tube can be filled with a liquid.

In another embodiment, the filament is at least partially inserted into the first tube on a first side of the drive mechanism and at least partially inserted into a second tube on a second side of the drive mechanism, whereby movement of the drive mechanism in a first direction causes corresponding linear movement and insertion of the filament into the first tube and retraction of the filament from the second tube.

In yet another embodiment, a first inlet valve is in fluid communication between the first tube and an inlet port and a second inlet valve is in fluid communication between the second tube and the inlet port. A first outlet valve is in fluid communication between the first tube and an outlet port and a second outlet valve is in fluid communication between the second tube and the outlet port.

In still another embodiment, the first and second outlet valves comprise a bi-directional valve.

In another embodiment, a fill port and a patient port are in fluid communication with the tube.

In yet another embodiment, a first check valve is in fluid communication between the fill port and the tube and a second check valve is in fluid communication between the patient port and the tube.

In another embodiment, insertion of the filament into the tube causes a vacuum in the tube to open the first check valve and draw fluid through the fill port while simultaneously pressurizing the second check valve into a closed position.

In yet another embodiment, retraction of the filament from the tube causes pressure within the tube adjacent the first and second check valves thereby causing the second check valve to open to force fluid from the tube through the second check valve and out the patient port while simultaneously pressurizing the first check valve into a closed position.

In another embodiment, a sheathing covers the tube to prevent the tube from being crushed.

The pump of the present invention has many advantages over the prior art. First, the pump of the present invention can provide very accurate dosing. The tube may be sufficiently long such that the system will have the accuracy of a very long syringe. For example for 1 mL, if the filament has a diameter of 0.0625 inch then the required tube length is 19.891 inches long for which a 20 inches long tube may be use. If the drive mechanism moves with an accuracy of +/−0.05 inch, the corresponding accuracy is +/−0.25%. Indeed, tube compliance will have more of an effect on accuracy than the driver mechanism.

Second, there is little or no waste of the drug being administered. The filament will slowly move forward in the tube until it reaches the injection site of the patient. As a result the only amount of the drug not delivered to the patient will be the film of drug left on the inside wall surface of the tube and any small amount that remains in the injection device at the injection site.

Third, the pump is inexpensive to manufacture and any disposable components of the pump are relatively inexpensive. In addition, the disposable components are small, creating less bio-hazardous waste, and can generally be made from typical medical materials, such as polyethylene, polycarbonate, polyvinylchloride or other materials known in the art. The disposable portion may include only the tube, the filament seal, the filament and the connector to the drive mechanism. All of these components are inexpensive devices. In the above example, the disposable components would include 20 inches of tubing, 22 inches of filament, a 001 size or similar O-ring, the connector to the drive mechanism, a pressure relief valve, and the exit port or the optional inlet port with check valve. In 2018 U.S. dollars these components should have a manufacturing cost of less than $10.

BRIEF DESCRIPTION OF THE DRAWINGS

The following detailed description of the illustrated embodiments is better understood when read in conjunction with the appended drawings. For the purpose of illustrating the invention, there is shown in the drawings exemplary embodiments which illustrate what is currently considered to be the best mode for carrying out the invention, it being understood, however, that the invention is not limited to the specific methods and instruments disclosed. In the drawings.

DETAILED DESCRIPTION OF THE ILLUSTRATED EMBODIMENTS

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices and technologies to which the disclosed inventions may be applied. Thus, the full scope of the invention is not limited to the examples that are described below.

Figure 1:
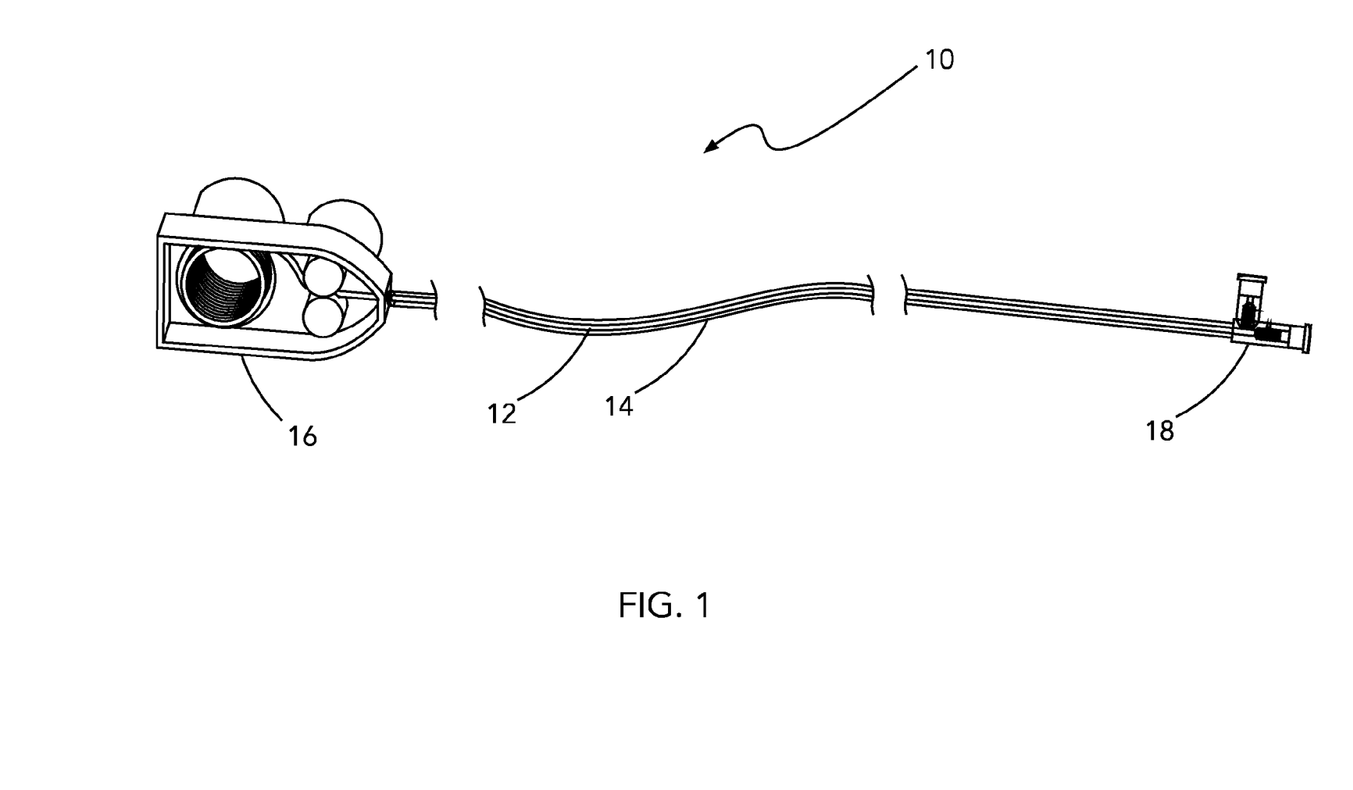
FIG. 1 is a perspective side view of a first embodiment of a pump in accordance with the principles of the present invention.

FIG. 1 illustrates a pump, generally indicated at 10, which may function as an infusion pump, for precise and controlled delivery of medications or other liquid substances at very low dosage rates. The pump 10 is comprised of a filament 12 that is extendable and retractable inside a drug delivery tube 14. The filament 12 acts as a syringe that can force the flow of a drug inside the tube 14 to a patient. The filament 12 and associated tube 14 acts like a syringe that is driven by a drive mechanism 16, such as a stepper motor, servo motor or other linear drive device that can accuracy control the movement of the filament 12 relative to the tube 14. The drive mechanism 16 may be coupled to a gear box reduction for increased accuracy of filament 12 movement and thus drug delivery accuracy. Specifically, the drive mechanism 16 moves the filament 12 through the tube 14 with linear accuracy. At the distal end of the tube 14, a coupler 18 is attached thereto for connection to an injection port of a patient (not shown).

The filament 12 includes a scale (e.g., Vernier) printed on its outer surface. The filament 12 can thus act as a linear encoder that can be read by optical or other sensors to provide feedback of the filament's position relative to the tube 14 and thus confirm the dosage of the drug provided to the patient accordingly.

Figure 2:
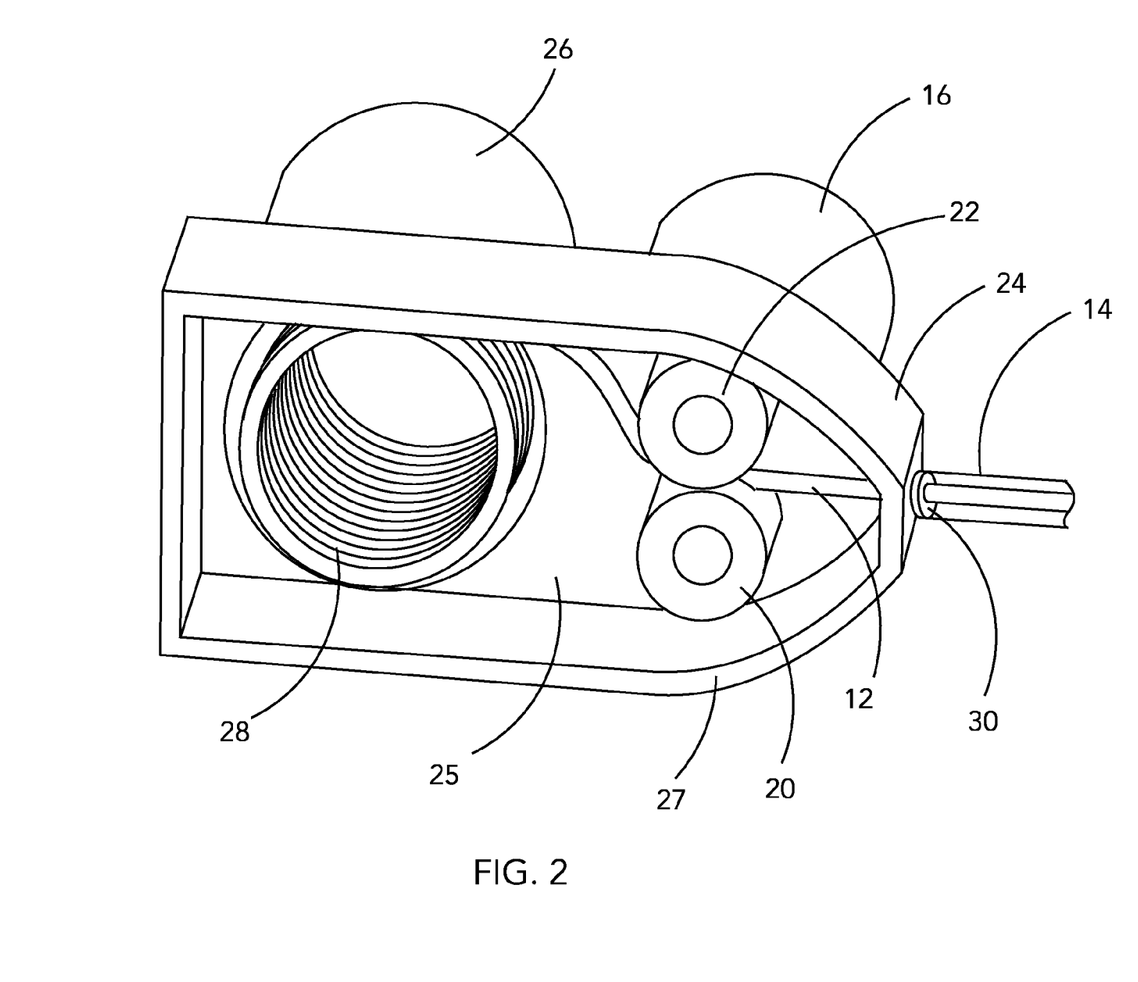
FIG. 2 is a partial perspective side view of the drive mechanism of the pump illustrated in FIG. 1.

As shown in FIG. 2, the filament 12 engages a secondary wheel 20, in the form of an idle wheel, that moves as the filament 12 moves, causing the secondary wheel 20 to rotate. The rotation of the secondary wheel 20 confirms that the filament 12 is actually moving and not slipping as the drive mechanism 16 and associated drive wheel 22 moves the filament 12. The filament 12 passes between the drive wheel 22 and the secondary idler wheel 20 and is engaged therein between such that, by frictional contact, as the drive wheel 22 moves, the filament 12 and correspondingly the idler wheel 20 also move, with the filament 12 being linearly advanced through the tube 14 and the idler wheel 20 being forced to rotate as the filament 12 is advanced.

The drive mechanism 16 is coupled to a housing 24. The housing 24 includes a back wall 25 containing a filament container 26 for retaining a spool 28 of unused filament 24. The tube 14 is coupled to the housing 24. A sliding filament seal 30 is position at an aperture in the housing side wall 27. The housing may be removably attached to the drive mechanism 16 so that the housing and associated filament can be discarded after a single use.

The sliding filament seal 30 is provided between the filament and the proximal end of the tube 14 closest to the drive mechanism 16. The seal 30 prevents the drug from escaping the proximal end of the tube 14.

Figure 3:
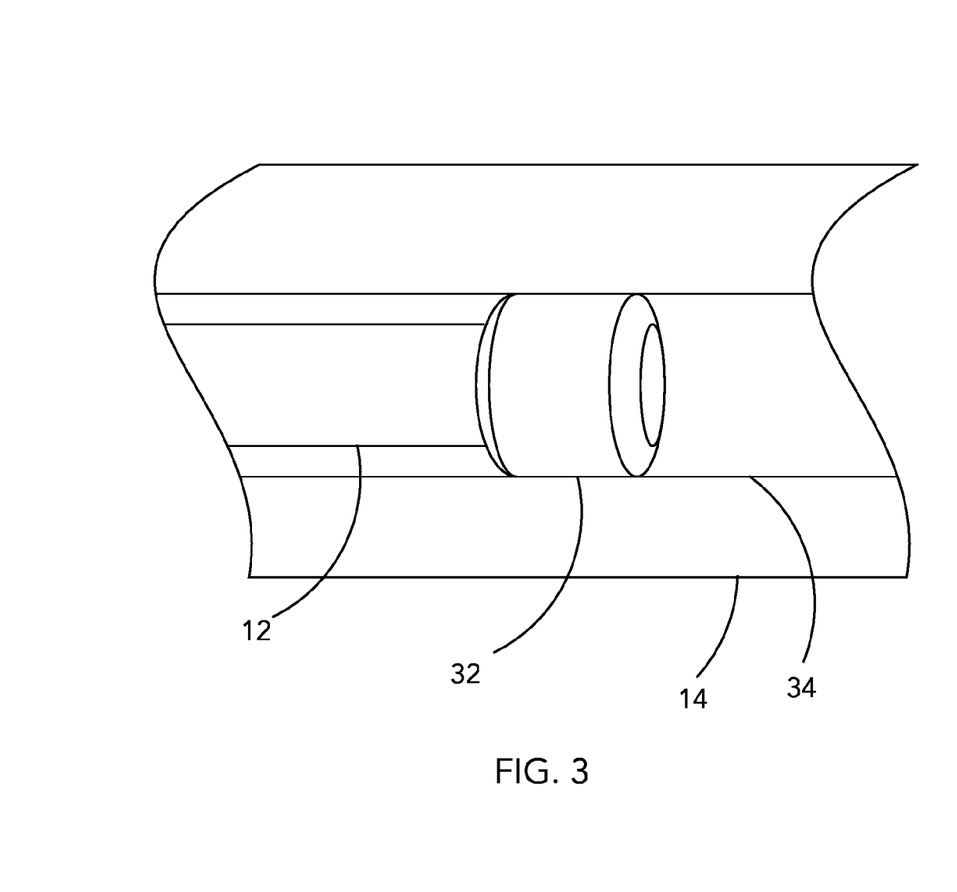
FIG. 3 is a partial perspective side view of the distal end of a filament of the pump illustrated in FIGS. 1 and 2.

As shown in FIG. 3, an external seal 32 is provided on the distal end of the filament 12, such as a plunger or O-ring on the distal end of the filament farthest from the drive mechanism 16. The seal 32 provides a liquid tight seal between the distal end of the filament 12 and the inner wall 34 of the tube 12. The seal 32 in combination with the filament 12 essentially forms a plunger that engages with the inner wall 34, much in the same way as a syringe plunger engages the inner wall of a syringe barrel. The liquid-tight seal between the inner wall 34 and the seal 32 prevents liquid from passing between the seal 32 and the inner wall 34. As the filament 12 is forced through the tube 14 in a direction toward the seal 32, any fluid contained within the tube 14 on the opposite side of the seal 32 is forced through the tube 14.

Figure 4:
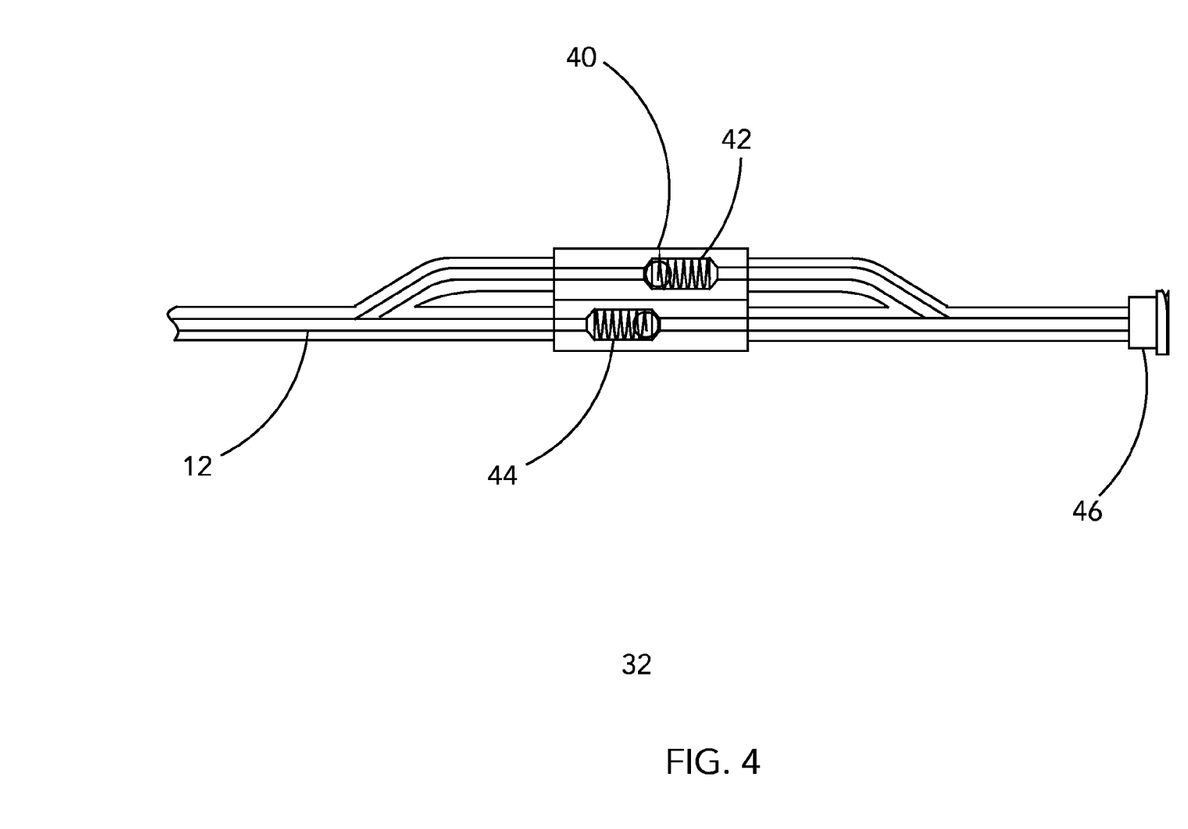
FIG. 4 is a partial perspective side view of a bi-directional valve assembly for the pump in accordance with the principles of the present invention.

As shown in FIG. 4, the distal end of the tube 14 is connect to the patient through a bi-directional pressure relief valve, generally indicated at 40. The pressure relief valve may have approximately 5 psi relief. The pressure relieve valve 40 includes a pressure relieve valve 42 for inward flow and a pressure relief valve 44 for outward flow arranged in serial. A Luer lock fitting 46 or other type of tube fitting known in the art is attached to the distal end of the tube extending from the pressure relief valve 40 for attachment to a patient's injection site.

Figure 5:
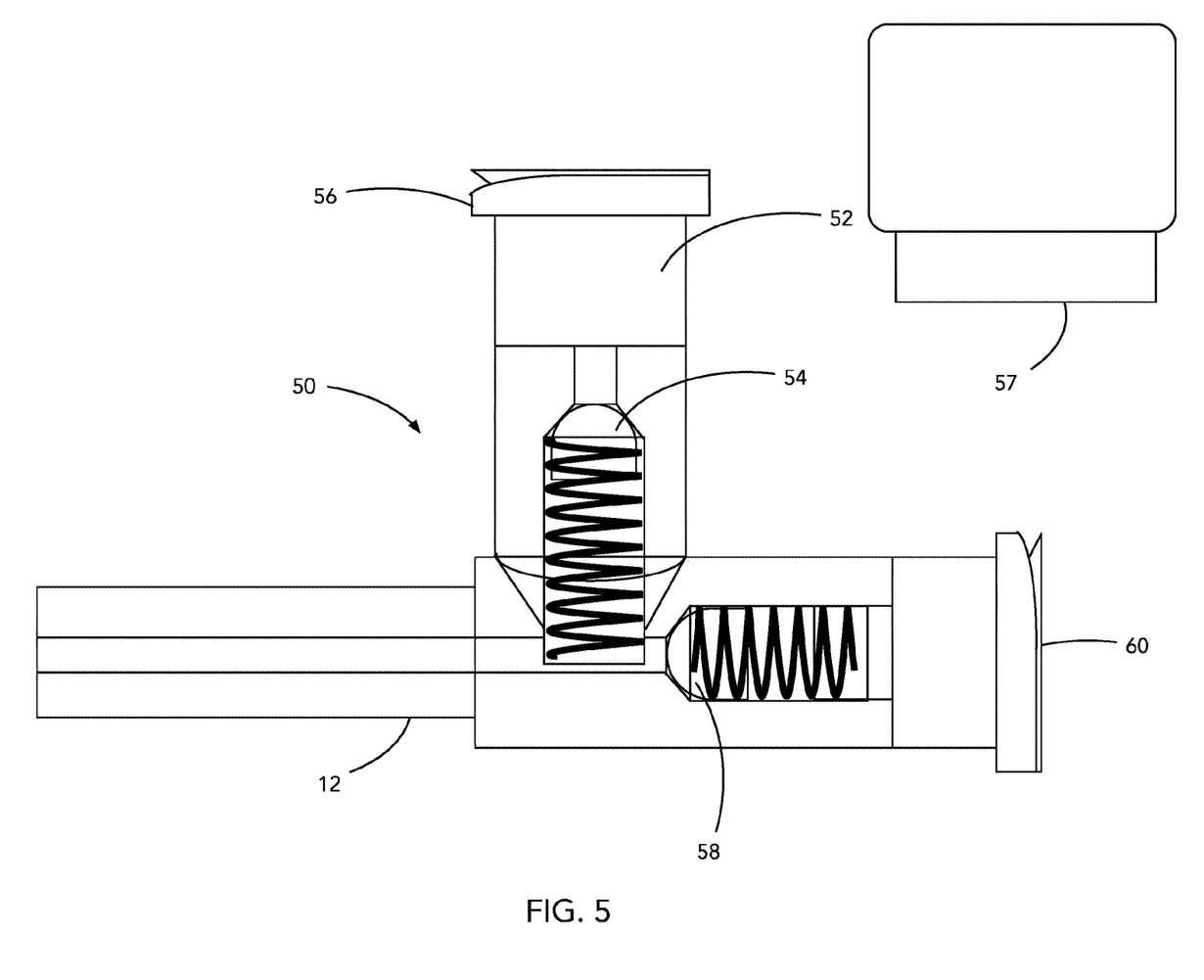
FIG. 5 is a partial perspective side view of a unidirectional valve assembly for the pump in accordance with the principles of the present invention.

Alternatively, as shown in FIG. 5, the distal end of the tube 12 may be connected to a unidirectional relief valve, generally indicated at 50, with an additional port 52 through a check valve 54 coupled to a separate fitting 56 forming a filling port where the system can be filled. A pressure relieve valve out 58 is coupled to the patient port 60, which may comprise a Luer lock fitting. The check valve 54 and pressure relieve valve 58 are comprised of spring biased ball valves. The springs are calibrated to require a specific pressure to cause the valve to open (e.g., 5 psi). The pressure relief valves can only be triggered at an elevated pressure such that body fluids from the patient cannot leak back into the system.

When the tube 12 is completely filled with the filament 14, the connection end fitting 56 of the tube check valve 54 is connected to the vial 57 of drug. The drive mechanism then pulls the filament backwards through the tube. Due to the use of the check valve 54, the vacuum required to pull fluid into the tube is directly a function of the pressure rating of the check valve 54. Once the tube 12 is filled with drug, the vial 57 is removed from the check valve port 52 and capped. The pump is now ready to be used or can be stored in a refrigerator or in whatever condition the drug requires.

The pump filled with drug can be stock piled in the refrigerator such clinicians administering the drug remove a package from the refrigerator, open the package, remove the pump system from the package, connect the system via the pressure check valve out to the patient and press start.

Alternatively, a separate port is provided that has a mechanically controlled valve that allows for filling the tube. A mechanically controlled device that overrides the output check valve allows fluid to flow into the system.

As previously mentioned, it is contemplated that the drive mechanism 16 shown in FIGS. 1 and 2 may be a separate device that is durable with the tube 14 and associated filament 12 and housing 24 being disposable in order to minimize the cost of the disposable components of the system. Alternatively, the drive mechanism 16 may be disposable as well.

The pump 10 of the present invention is coupled to an injection site of the patient. The injection site may be vascular, subcutaneous or other injection site types known in the art. The injection site (not shown) includes a disconnect fitting to which the tube 14 of the present invention connects. As shown in FIG. 5, the distal end of the tube 14 includes a check valve 58 to prevent a flow of fluid from the patient when the pump tube is disconnected.

The pump can either be provided with the drug prefilled in the tube with the filament retracted within the tube or ready to be filled with the filament fully extended into the tube. To fill the pump, the distal end of the tube is coupled to a vial of the desired drug. The drive mechanism pulls the filament through the tube retracting it into the pump housing thus forming a vacuum in the tube. When the vacuum pressure exceeds the limit of a pressure relief valve, the drug is drawn into the tube behind the distal end of the tube. Once the tube is completely filled or the drug in the vial has been completely drawn into the tube, the tube is disconnected from the vial. The pump is then ready to be used or can be stored as required by the drug manufacturer's recommendations, such as in a refrigerator.

Prefilled pumps with a drug can be placed in packages and stored in a refrigerator so that clinicians can take a package from the refrigerator, open the package, remove the pump/drug system from the package, attached the pump tube to the patient and start the pump.

The pump system can be battery powered with the battery housed within the housing of the drive mechanism. The housing may also house the electronics in addition to the drive mechanism. In this case, the housing and all of its components can be dispensed after the pump has been used. Alternatively, the pump housing may contain the electronics and drive mechanism as reusable components with the tubing and filament contained in a separate disposable cartridge that is discarded after a single use.

The fusion pump of the present invention has many advantages over the prior art. First, the pump of the present invention can provide very accurate dosing. The tube may be sufficiently long such that the system will have the accuracy of a very long syringe. For example for 1 mL, if the filament has a diameter of 0.0625 inch then the required tube length is 19.891 inches long for which a 20 inches long tube may be use. If the drive mechanism moves with an accuracy of +/−0.05 inch, the corresponding accuracy is +/−0.25%. Indeed, tube compliance will have more of an effect on accuracy than the driver mechanism.

Second, there is little or no waste of the drug being administered. The filament will slowly move forward in the tube until it reaches the injection site of the patient. As a result the only amount of the drug not delivered to the patient will be the film of drug left on the inside wall surface of the tube and any small amount that remains in the injection device at the injection site. That is, the pump of the present invention is capable of delivery nearly 100% of the drug. For example, for a tube to the patient having an inner diameter of 0.04 inch and being 2 inches long, the volume is 0.00251 cubic inches or 0.041 mL. The total injection amount is 1 mL. Thus, the waste of 0.041 mL is only 4.1% of the total drug volume. Moreover, the longer the tube, the greater the percentage of drug delivered to the patient since the piston is squeegeeing the walls of the tube as it sends the drug to the patient.

Third, the pump of the present invention is linearly accurate. For example, with movement of +/−0.05 inch increments of a 20 inch long tube, the linear accuracy is +/−0.2%.

Fourth, the pump is inexpensive to manufacture and any disposable components are cheap. The disposable portion may include only the tube, the filament seal, the filament and the connector to the drive mechanism. All of these components are inexpensive devices. In the above example, the disposable components would include 20 inches of tubing, 22 inches of filament, a 001 size or similar O-ring, the connector to the drive mechanism, a pressure relief valve, and the exit port or the optional inlet port with check valve. In 2018 U.S. dollars these components should have a manufacturing cost of less than $10. In addition, the disposable components per pump are relatively small compared to other systems known in the art, thus generating fewer biohazardous materials requiring disposal. These components can generally be made from typical medical materials, such as polyethylene, polycarbonate, polyvinylchloride or other materials known in the art.

In addition to driving the filament in a single direction, a pump according to the present invention can be configured for reciprocal operation. That is, the pump is capable of moving the filament in either direction through the tube. The distal end of the tube is coupled to a set of in and out check valves. When the driver draws the filament back through the tube, it will pull fluid in from a reservoir through the inlet check valve. When the driver pushes the filament into the tube, it will push the fluid out the outlet check valve. Thus, the pump can be localized at a distance from the driver or it can be all in a single package. This also provides a highly accurate pump as it is a syringe-type pump with a very long stroke compared to its diameter.

Figure 6:
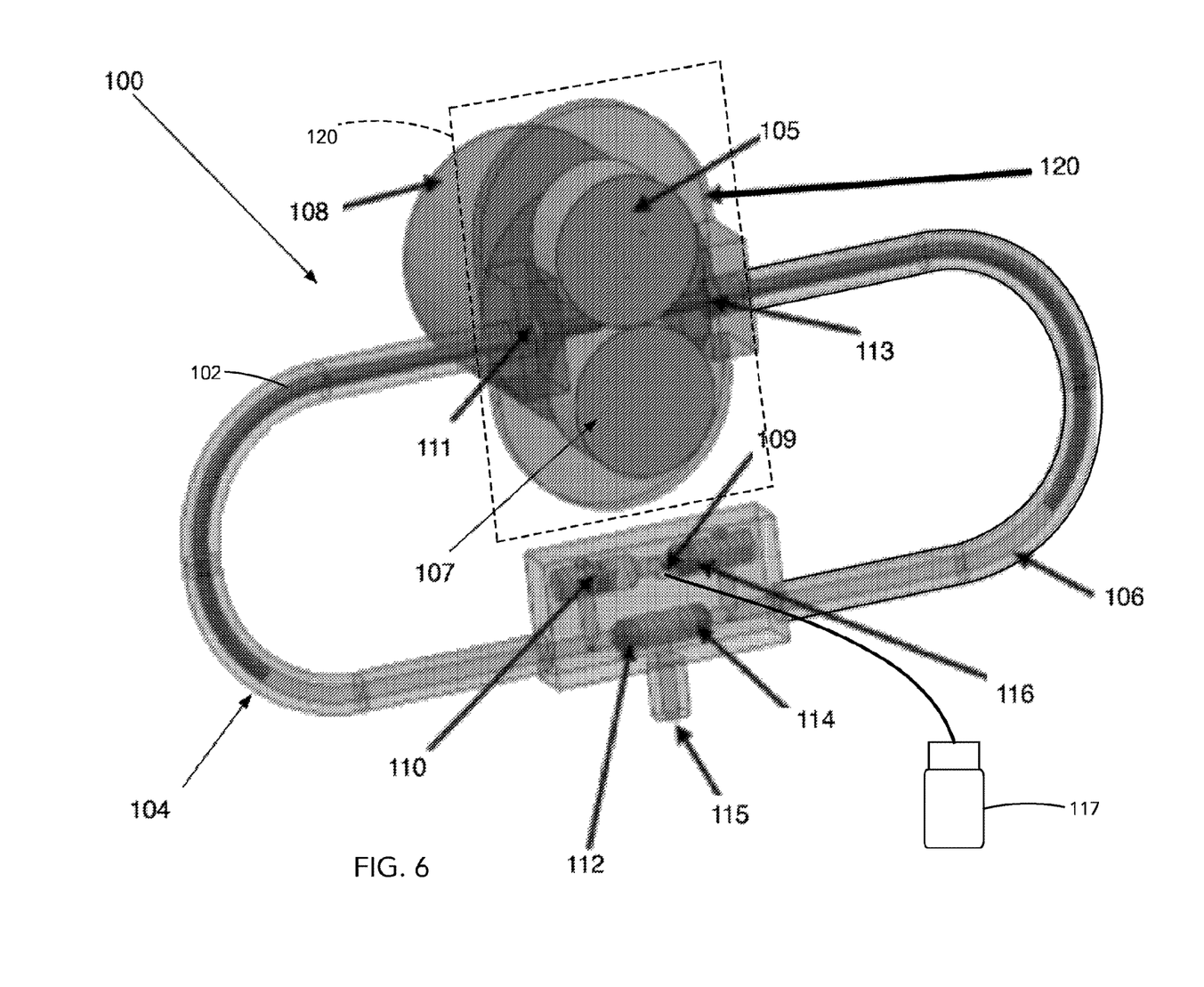
FIG. 6 is a perspective side view of a second embodiment of a pump in accordance with the principles of the present invention.

As shown in FIG. 6, such a reciprocating pump that can drive the filament in either direction, generally indicated at 100, provides two opposing pumps in tandem. In this configuration, when one pump is on an intake stroke the other one is on an output stroke. Since the motor speed is directly related to the flow, the flow rate is extremely constant with only occasional millisecond pauses when the motor changes directions at the end of each stroke. The pump 100 is capable of moving the filament 102 with the drive wheels 105 and 107 in either direction through first and second tubes 104 and 106. Each distal end of the first and second tubes 104 and 106 are coupled to a respective first and second set of in and out check valves. The proximal ends of the tubes 104 and 106 are provided with seals around the filament 102. When the driver 108 draws the filament 102 back through the tube 104, it will pull fluid in from a reservoir 117, through the inlet port 109 and through the inlet check valve 110. When the driver pushes the filament 102 into the tube 104, it will push the fluid out the outlet check valve 112. Simultaneously, when the driver 108 pushes the filament 102 through the tube 106, it will force fluid out the outlet check valve 114 and through the patient port 115. The outlet check valves 112 and 114 comprise a bi-directional check valve in which it can let fluid from either the tube 104 or the tube 106 through the outlet patient port 115 depending on which tube 104 or 106 is pressurized sufficiently to open the valve. Each check valve 109, 110, 112 and 114 are spring biased ball valves positioned within a respective fluid flow line of the pump 100. When the driver 108 pulls the filament 102 through the tube 106, it will draw fluid in from the reservoir 117, through the inlet port 109, through the inlet check valve 116 and into the tube 106. The housing 120, indicated by dashed lines, contains the drive wheels 105 and 107, the filament seals 111 and 113.

Figure 7:
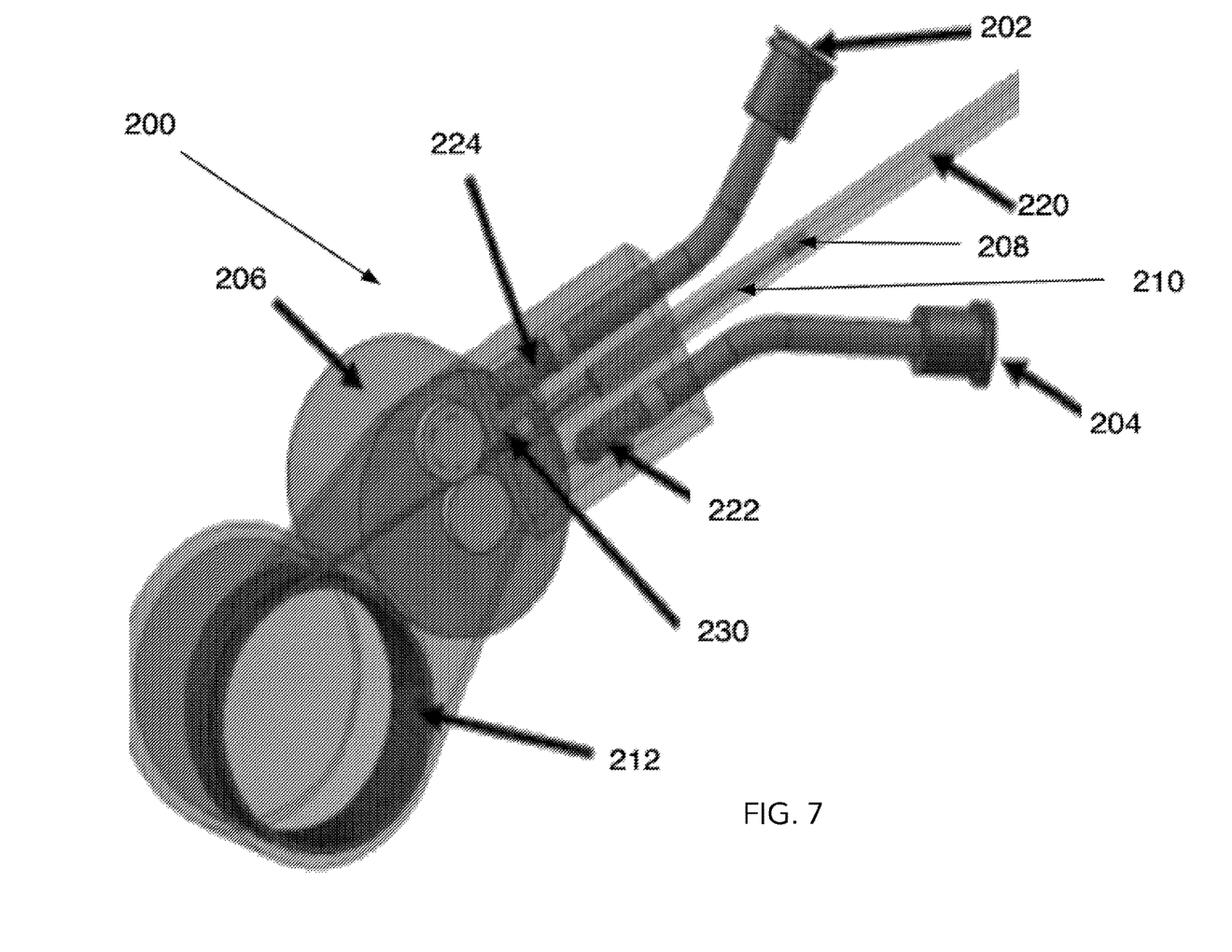
FIG. 7 is a partial perspective side view of a third embodiment of a pump in accordance with the principles of the present invention.

As shown in FIG. 7, a pump, generally indicated at 200 and in accordance with the principles of the present invention, may include a fill port 202 and a patient port 204 that are proximate to the drive mechanism 206. In this embodiment, the drug is contained above the filament head 208 such that as the filament 210 is retracted into the filament container 212 by the drive mechanism 214 and associated drive wheels 216 and 218, the drug is drawn toward the proximal end of the tube 220 and can flow out through the check valve 222 and through the patient port 204. Conversely, to fill the tube, the fill port 202 is coupled to a drug supply, such as a drug in a vial or a bag. As the filament is extended into the tube 220, the drug is drawn through the check valve in 224 and into the tube 220 above the filament head 208. The filament head 208 has a diameter that allows the filament head 208 to work as a syringe plunger by forming a fluid tight seal between the inner wall of the tube 220 and the filament head. The body of the filament 220 is of a smaller diameter to allow the drug to be drawn into the tube 220 around the body of the filament. A filament seal 230 is provided at the proximal end of the tube 220 to prevent the flow of the drug from flowing out of the valve assembly. The volume of the drug in the tube can be easily calculated by subtracting the volume of the filament body from the inner volume of the tube within the portion of the tube that the drug has filled.

It should be noted that the size of the pump can be relatively small with the drive motor being approximately 1 inch in diameter and the tube extending 20 inches or more depending on the desire dosage of the drug to be administered.

The various pumps according to the principles of the present invention can be localized at a distance from the driver or it can be all in a single package. This also provides a highly accurate pump as it is a syringe-type pump with a very long stroke compared to its diameter.

It if further contemplated that a pump according to the present invention could also be used to impregnate a fluid into a surface. For example, the filament could push through the check valve and into or onto a surface. Thus, tiny drops of fluid could be placed onto a surface or even injected into a surface.

The pump of the present invention can also be configured for nonmedical fluid delivery. For example, there are many expensive epoxies and other fluids that require accurate delivery and then disposal of items that come into contact with the fluid. In an epoxy system, two or more of these delivery devices could be coupled to the same durable driver, coupled to a separate durable driver, or coupled to a disposable driver. The long tubes allow for a pen like end the user can manipulate while the driver sits on a surface at some distance away.

Furthermore, the pump valve may be positioned at the injection site with the filament reciprocating with pump valves near the injection side.

The pumping could also occur inside the body of the patient with the drive mechanism being external to the body.

The pump can use very long tubes to provide a large surface area to volume, which may be particularly useful for dialysis with a pump provided inside a dialysate permeable tube.

The pump according to the present invention may also be used in multiples in certain applications.

The pump of the present invention may also be used for moving fluid through test chambers. Because fluid can be accurately moved over a long distance, and there is significant surface area in the tube compared to volume of fluid, the device could be used to make a system that does multiple tests on a volume of fluid. The filament could move the fluid from one chamber to the next.

While disclosed with reference to certain illustrative embodiments herein, the pump of the present invention may have other configurations. For example, the filament can be coupled to a crank instead of drive wheels as shown and described herein. Alternatively, ratchet mechanism could be used to drive the filament. Likewise, an inexpensive drive mechanism such as a solenoid could drive the filament. Moreover, the filament could protrude into the injection-into-patient tubing.

Figure 8:
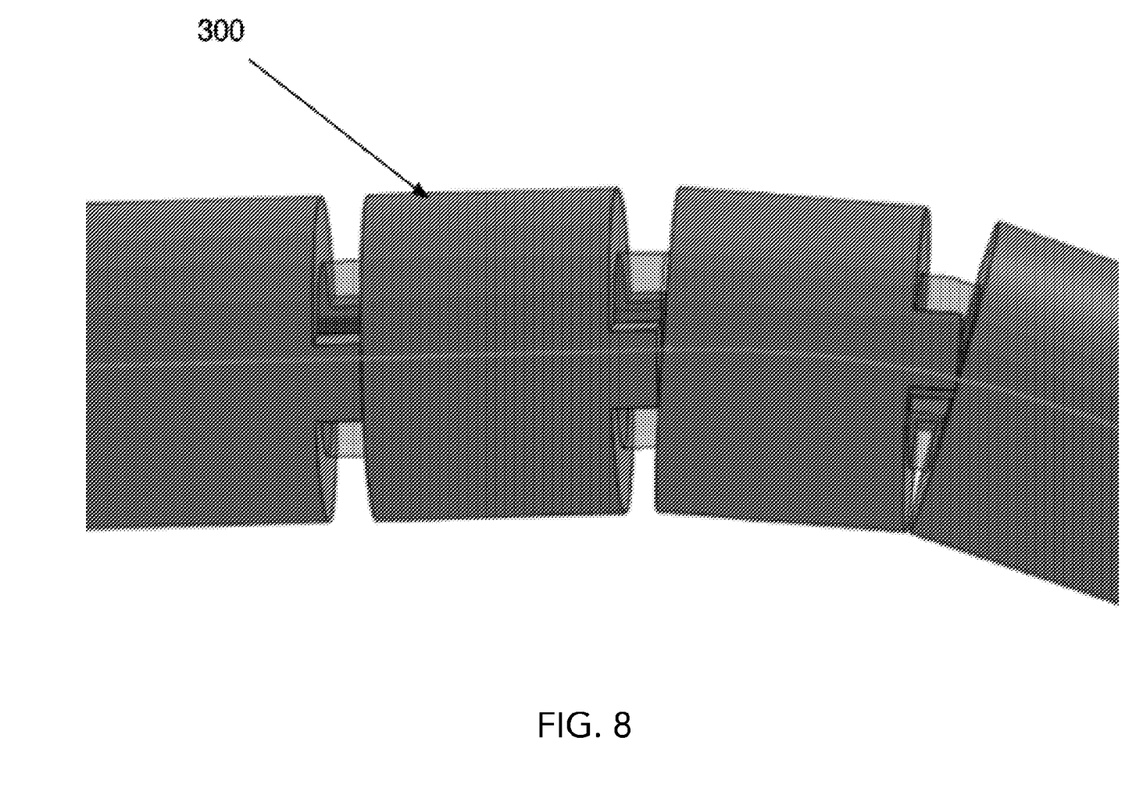
FIG. 8 is a partial perspective side view of a sheathing for the tubing of the pump in accordance with the principles of the present invention.

Since the tube may comprise the reservoir as herein described, free flow of the drug is not possible since it isn't possible to create up stream pressure. If the tube is very flexible, upstream pressure could be made by crushing the tube. Since there is an exit pressure relief valve, the tube would have to be crushed with greater force than the exit pressure. Sheathing would also eliminate this problem. To prevent such crushing, a sheathing 300 as shown in FIG. 8 may provide a hard shell over the tubing. The sheathing 300 can be space so that the tubing still has loose flexibility, but rigid limits to radius of bend. The sheathing eliminates the ability to crush the tube. Alternatively, the tubing could also be coiled and put inside a case such that the pump is like a cell phone sized device that is strapped to the patient near the injection site.

Accordingly, the pump of the present invention is capable of providing:

Super slow flow rates (1 mL/day);
Super high accuracies (+/−1)
Less than 2% drug waste
Inexpensive disposable cartridge;
Particular applicability for biological drugs that must have all exposed materials thrown out each day;
Non-damaging application for large cell/molecule drugs; and
Good applicability for neonate drug delivery, including ability to draw from an IV bag.

Because the pump of the present invention can be so inexpensively manufactured, while achieving highly accurate and reliable volumetric drug delivery, the pump could be sold in combination with the drug in a single sterilized package. Moreover, the drug pump could be calibrated for delivery of a specific drug requiring specific dosing. That way, a doctor or other health care provider does not need to program the delivery system. Simply activating the drug delivery system will dispense the drug according to the proper dosing requirements.

It is contemplated, and will be apparent to those skilled in the art from the foregoing specification, drawings, and examples that modifications and/or changes may be made in the embodiments of the invention. Accordingly, it is expressly intended that the foregoing are only illustrative of preferred embodiments and modes of operation, not limiting thereto, and that the true spirit and scope of the present invention be determined by reference to the appended claims.

While the present invention has been described with reference to certain illustrative embodiments to illustrate what is believed to be the best mode of the invention, it is contemplated that upon review of the present invention, those of skill in the art will appreciate that various modifications and combinations may be made to the present embodiments without departing from the spirit and scope of the invention as recited in the claims. The claims provided herein are intended to cover such modifications and combinations and all equivalents thereof. Reference herein to specific details of the illustrated embodiments is by way of example and not by way of limitation.

Thus, aspects and applications of the invention presented here are described in the drawings and in the foregoing detailed description of the invention. Those of ordinary skill in the art will realize that the description of the present invention is illustrative only and not in any way limiting. Other embodiments of the invention will readily suggest themselves to such skilled persons including, without limitation, combinations of elements of the various embodiments. Various representative implementations of the present invention may be applied to any valve.

Unless specifically noted, it is intended that the words and phrases in the specification and the claims be given their plain, ordinary, and accustomed meaning to those of ordinary skill in the applicable arts. It is noted that the inventor can be his own lexicographer. The inventor expressly elects, as his own lexicographer, to use the plain and ordinary meaning of terms in the specification and claims unless they clearly state otherwise in which case, the inventor will set forth the "special" definition of that term and explain how it differs from the plain and ordinary meaning. Absent such statements of the application of a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified or narrowed in some way, then such noun, term or phrase will expressly include additional adjectives, descriptive terms or other modifiers in accordance with the normal precepts of English grammar. Absent the use of such adjectives, descriptive terms or modifiers, it is the intent that such nouns, terms or phrases be given their plain, and ordinary English meaning to those skilled in the applicable arts as set forth above.

Further, the inventor is fully informed of the standards and application of the special provisions of 35 U.S.C. § 112(f). Thus, the use of the words "function," "means" or "step" in the Detailed Description of the Invention or claims is not intended to somehow indicate a desire to invoke the special provisions of 35 U.S.C. § 112(f) to define the invention. To the contrary, if the provisions of 35 U.S.C. § 112(f) are sought to be invoked to define the inventions, the claims will specifically and expressly state the exact phrases "means for" or "step for" and the specific function (e.g., "means for heating"), without also reciting in such phrases any structure, material or act in support of the function. Thus, even when the claims recite a "means for . . . " or "step for . . . " if the claims also recite any structure, material or acts in support of that means or step, or that perform the recited function, then it is the clear intention of the inventor not to invoke the provisions of 35 U.S.C. § 112(f). Moreover, even if the provisions of 35 U.S.C. § 112(f) are invoked to define the claimed inventions, it is intended that the inventions not be limited only to the specific structure, material or acts that are described in the illustrated embodiments, but in addition, include any and all structures, materials or acts that perform the claimed function as described in alternative embodiments or forms of the invention, or that are well known present or later-developed, equivalent structures, material or acts for performing the claimed function.

What is claimed is:

1. A pump, comprising:
   a drive mechanism;
   a first tube coupled to the drive mechanism;
   a filament coupled to the first tube and extendable into the first tube by the drive mechanism;
   at least one check valve coupled to the first tube, wherein as the filament is forced by the drive mechanism into the first tube, fluid contained in the first tube is forced by the filament through the at least one check valve and out of the first tube; and
   a second tube, with the filament at least partially inserted into the first tube on a first side of the drive mechanism and at least partially inserted into the second tube on a second side of the drive mechanism, whereby movement of the drive mechanism in a first direction causes corresponding linear movement and insertion of the filament into the first tube and retraction of the filament from the second tube.

2. The pump of claim 1, wherein the drive mechanism comprises a motor coupled to at least one drive wheel, the at least one drive wheel engaging the filament to drive the filament through the first tube.

3. The pump of claim 2, further comprising a second wheel proximate the at least one drive wheel with the filament passing between the at least one drive wheel and the second wheel and engaged between the at least one drive wheel and the second wheel such that rotation of the at least one drive wheel causes advancement of the filament and rotation of the second wheel.

4. The pump of claim 1, further comprising a filament seal positioned proximate a proximal end of the first tube, the filament seal providing a seal around the filament and preventing fluid within the first tube from passing out of the proximal end of the first tube.

5. The pump of claim 1, further comprising a housing having a filament container, the filament arranged in a spool of unused filament within the filament container.

6. The pump of claim 1, wherein the one or more check valves further comprises a bi-directional pressure relief valve, the bi-directional pressure relief valve comprising a first pressure relief valve for inward flow and a second pressure relief valve for outward flow.

7. The pump of claim 1, further comprising a uni-directional pressure relief valve coupled to a distal end of the first tube, the uni-directional pressure relief valve comprising a first pressure relief valve for outward flow through a patient port.

8. The pump of claim 7, wherein the one or more check valves further comprises a check valve for inward flow coupled to a filling port through which the first tube can be filled with a liquid.

9. The pump of claim 1, further comprising first and second inlet valves, the first inlet valve in fluid communication between the first tube and an inlet port, the second inlet valve in fluid communication between the second tube and the inlet port and further comprising a first outlet valve and a second outlet valve, the first outlet valve in fluid communication between the first tube and an outlet port and the second outlet valve in fluid communication between the second tube and the outlet port.

10. The pump of claim 9, wherein the first and second outlet valves comprise a bi-directional valve.

11. The pump of claim 1, further comprising a fill port and a patient port in fluid communication with the first tube.

12. The pump of claim 11, wherein the at least one check valve comprises a first check valve in fluid communication between the fill port and the first tube and a second check valve in fluid communication between the patient port and the first tube.

13. The pump of claim 12, wherein insertion of the filament into the first tube causes a vacuum in the tube to open the first check valve and draw fluid through the fill port while simultaneously pressurizing the second check valve into a closed position.

14. The pump of claim 13, wherein retraction of the filament from the first tube causes pressure within the first tube adjacent the first and second check valves thereby causing the second check valve to open to force fluid from the first tube through the second check valve and out the patient port while simultaneously pressurizing the first check valve into a closed position.

15. The pump of claim 1, further comprising a sheathing for covering the first tube to prevent the first tube from being crushed.

* * * * *